United States Patent [19]
Vikterlöf et al.

[11] Patent Number: 4,679,076

[45] Date of Patent: Jul. 7, 1987

[54] MEANS FOR REGISTERING COORDINATES

[76] Inventors: Karl-Johan Vikterlöf, Vårbovägen 14, 702 30 Örebro; Göte Palsgard, Eklundavägen 34 A, 702 17 Örebro, both of Sweden

[21] Appl. No.: 711,577

[22] PCT Filed: May 30, 1984

[86] PCT No.: PCT/SE84/00206

§ 371 Date: Feb. 8, 1985

§ 102(e) Date: Feb. 8, 1985

[87] PCT Pub. No.: WO84/04876

PCT Pub. Date: Dec. 20, 1984

[30] Foreign Application Priority Data

Jun. 8, 1983 [SE] Sweden ............................ 8303224

[51] Int. Cl.4 ............................................ H04N 7/18
[52] U.S. Cl. ...................................... 358/107; 358/93; 358/96; 356/376
[58] Field of Search .................. 358/107, 93, 101, 96; 356/376, 1, 381; 250/560; 382/22, 25

[56] References Cited

U.S. PATENT DOCUMENTS

| | | | |
|---|---|---|---|
| 3,976,382 | 8/1976 | Westby | 358/376 |
| 4,188,544 | 2/1980 | Chasson | 358/107 X |
| 4,343,553 | 8/1982 | Nakagawa et al. | 356/376 |
| 4,361,830 | 11/1982 | Honma et al. | 358/107 X |
| 4,406,544 | 9/1983 | Takada et al. | 356/376 |
| 4,498,778 | 2/1985 | White | 358/107 X |

FOREIGN PATENT DOCUMENTS 0062941 10/1982 European Pat. Off. .
0403321 8/1978 Norway .

Primary Examiner—Howard W. Britton
Assistant Examiner—Victor R. Kostak
Attorney, Agent, or Firm—Dennison, Meserole, Pollack & Scheiner

[57] ABSTRACT

The coordinates are determined for arbitrary points on the contour of any body (1). This is achieved by producing a line (13) circumventing the body (1). The circumferential line (13) is moved along the body (1) and is reproduced in various positions. In each position the coordinates along the circumferential line (13) are determined and stored in a memory unit (9), enabling them to be subsequently used for various purposes such as planning dosage, radiation and the like for said body (1), and for calculating distances of volumes prior to taking corrective measures.

10 Claims, 4 Drawing Figures

MEANS FOR REGISTERING COORDINATES

BACKGROUND OF THE INVENTION

The present invention relates to a means for registering coordinates and particularly to registering the coordinates for various points on the surface of an arbitrary body. The body may have any appearance whatsoever. Of particular interest are the surface coordinates of a living being such as a human. These coordinates can be used for evaluation and adjustment in the fields of medical radiology and surgery. The known method of obtaining various coordinates of the type just mentioned is to take measurements manually via direct contact. However, this is laborious and sometimes directly unsuitable. The desired accuracy is difficult to achieve.

SUMMARY OF THE INVENTION

The object of the present invention is to register the coordinates for arbitrary points on a body, preferably a human body, without manual intervention. The coordinates determined are then stored in a memory unit, the content of which can be used for making the desired calculations and presentations of the body with great accuracy.

Registered coordinates can also be of great value in the clothing industry since registered coordinates give the exact measurements of the body to be provided with a suit or other article of clothing. The coordinates in the memory unit can also be used to manufacture footwear, the coordinates of the foot being registered in said memory unit.

The coordinates for arbitrary points on the surface of a body, such as a human body, are most suitably obtained by the use of one or more means such as light sources generating a circumferential line about the body. The circumferential line may be complete or divided into sections. The body and the circumferential line are displaceable in relation to each other. The appearance of the circumferential line at each position along the body is reproduced by means of reproduction from one or several sides, for instance. The picture(s) obtained in one position are used to determine the coordinates along the circumferential line. The coordinates obtained are stored in the memory unit of a computer. A coordinate reference system is necessary to enable determination of the coordinates. Two coordinates are always obtained from the plane where the circumferential line is located. The third coordinate is obtained from the direction of displacement for the relative movement. The relative movement may be continuous or it may take place in steps.

In a preferred embodiment of the present invention two TV cameras are preferably used to reproduce the circumferential line. These cameras are located one of each side of the circumferential line and directed towards it, or directed in such a way that the circumferential line is reproduced within the field of vision of the TV cameras. The use of two cameras enables parts of the circumferential line which are hidden to one camera to be seen by the other. Obviously, if there are no parts hidden to either camera, then one is sufficient.

If two TV cameras are used they should preferably be arranged on one and the same line, said line being parallel to the direction of displacement for the relative movement between circumferential line and body. In the latter case, the two TV cameras may be directed towards each other or perpendicular to the direction of displacement.

Several pairs of TV cameras, each pair arranged on its own line, may be arranged around said body, the pairs being arranged at the same distance from a centre line parallel to the displacement line.

A number of light sources may also be arranged around said centre line, preferably equally spaced.

If desired, one camera in each pair may be replaced by a mirror arrangement.

All the TV cameras and light sources may be combined into a single unit in which the individual elements are stationary in relation to each other but the unit is movable in relation to the body. The body can then be displaced through the unit or it may remain stationary while the unit is moved.

According to another embodiment of the invention, both cameras and body may be stationary in relation to each other, while the circumferential line is displaced in relation to the body.

It is advisable to arrange the light source(s) generating the circumferential line, and the cameras, in such a way that the light source(s) generate(s) light of a certain frequency and the cameras are only sensitive to light of said frequency. The same effect is achieved by giving the circumferential line a light intensity which differs essentially from the light intensity of the surroundings and that the camera(s) only react(s) to the light intensity of the line. Since a circumferential line of the type mentioned generally has two edges it may be advisable to register only one edge of the circumferential line.

Each camera is suitably so designed that the reproduced circumferential line completely fills the field of vision of the camera.

The pictures intercepted by the TV cameras around the body are converted to a video signal which is supplied to a logical unit. In the logical unit the video signal is converted to a digital signal. The digital signal from the logical unit is supplied to a computer to which a signal which is a function of the relative movement between circumferential line and body is also supplied. In known manner the computer determines the three-dimensional coordinates for points along each circumferential line in relation to a programmed reference system. The coordinates calculated are supplied to a memory. The digital signal from the logical unit is also supplied to a monitor enabling the relevant picture to be observed there. The computer is also designed to calculate the coordinates for points located extremely close together along certain sections of the circumferential line and only for widely spaced points along other sections.

As mentioned earlier, the coordinates stored in the memory may have a multitude of uses. The memory unit can therefore be connected to apparatus able to utilize the coordinates registered.

Registered coordinates can also be transferred to separate memory units such as discs, thus enabling the memory to be used at a place separated from where the cameras and light sources are located. The memory can be moved to an operating theatre, for instance, or if it is to be used within the clothing industry it can be moved from a clothing shop to a tailor's.

To facilitate computer calculation of the coordinates in a three-dimensional system it may be advisable to use the interlacing technique, alternate pictures of the circumferential line being produced by odd lines and those between by even lines. With this method the number of points reproduced in each half of the circumferential line will be half the number reproduced without interlacing.

Cameras arranged in accordance with the interlacing technique can also be used to determine the distance to an arbitrary body. The two cameras must then be directed towards the body and when their interlace pictures overlap, which can be ascertained visually with great accuracy, the conditions for determining the distance have been achieved, since the distance between the two cameras is fixed and their angles to the base line can be determined. In determining the distance to the latter object, the two cameras may be hidden from each other. In the latter case the distance between the two cameras should have been determined in one way or another.

In the latter case where the body had easily detectable details, the system permits coordinate determination without the use of a separately generated circumferential line. Thus the system can also provide speed information by means of consecutive position determination.

It is mentioned above that the body may be of any arbitrary shape. Examples of bodies other than human bodies are automobiles, propellers, flat surfaces such as roads and lifting cranes, etc.

A description is given above of how the coordinates are determined for an external surface. It should be evident that the invention is also applicable for determining the coordinates for points on an internal surface. Examples of such internal surfaces are tunnel walls, the walls of a room and the inner surface of a pipe or tube.

Additional characteristics of the present invention are revealed in the following claims.

BRIEF DESCRIPTION OF THE DRAWINGS

One of various applications according to the present invention will be described in more detail with reference to the accompanying four drawings in which.

DESCRIPTION OF THE PREFERRED EMBODIMENTS

Figure 1:
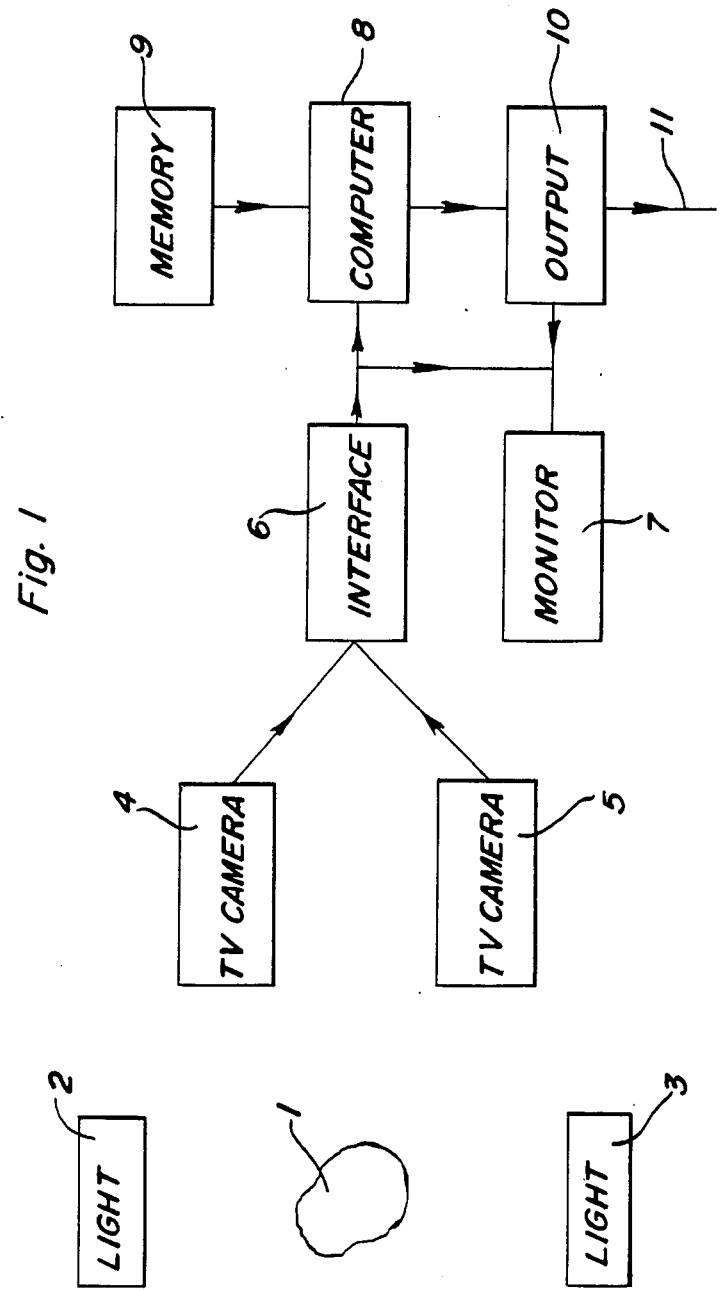
FIG. 1 shows a block diagram for the means according to the invention.

In FIG. 1, 1 is a body, which may be a human body. A slot light source 2 and 3, respectively, is arranged on each side of the body 1. The slot light source may be of make Therados Las II. The two slot light sources 2 and 3 generate a circumferential line around the body 1. The circumferential line may be extremely narrow or it may be wide enough to detect a front and a rear edge line.

Figure 2:
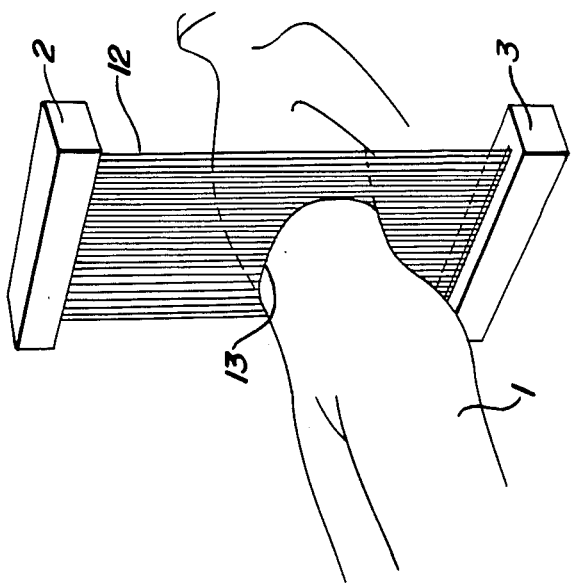
FIG. 2 shows a means for generating a circumferential line.

The two slot light sources 2 and 3 substantially generate a light curtain 12 (see FIG. 2). The light generating the circumferential line may suitably be such that the line contrasts extremely sharply with the surroundings. The light generating the circumferential line may also have a wave-length lying within a selected range, such as between wavelengths A and B. Two TV cameras are arranged to photograph the circumferential line of the object. These TV cameras may be of make Hitachi, Type KP-120. The two TV cameras 4 and 5 are connected to an interface unit 6 built up of conventional IC circuits, FIFO circuits of TRWTDC 10 30 36 type and D/A converters of National Semiconductor DAC 0831 type, which convert the video signals generated by the two TV cameras to a digital signal. Said signal is then transmitted to a monitor 7 of make Hitachi VM-906A, for instance, and to a computer 8 of make Intel 80186, for instance. The picture registered primarily by the TV cameras 4 and 5 can be reproduced in the monitor 7 if desired. The computer 8 is programmed to enable the coordinates in an arbitrarily selected reference system of points along the circumferential line to be calculated. The positions of the projected circumferential line are taken into consideration in this calculation. The circumferential line defines a plane which can be displaced, preferably along its normal. The distance between the coordinate points along the line can be selected by means of a suitable polygon program. This procedure may reduce the memory capacity requirement.

The coordinates for the points on the circumferential line are transmitted from computer 8 to memory unit 9, composed of a number of Intel 2164 As for instnce. The computer 8 has an output 10 from which registered coordinates are transmitted at 11 to a portable memory unit (not shown) such as a disc, or some form of apparatus which can utilize the registerd coordinates such as a monitor, printer, external computer or the like.

Figure 3:
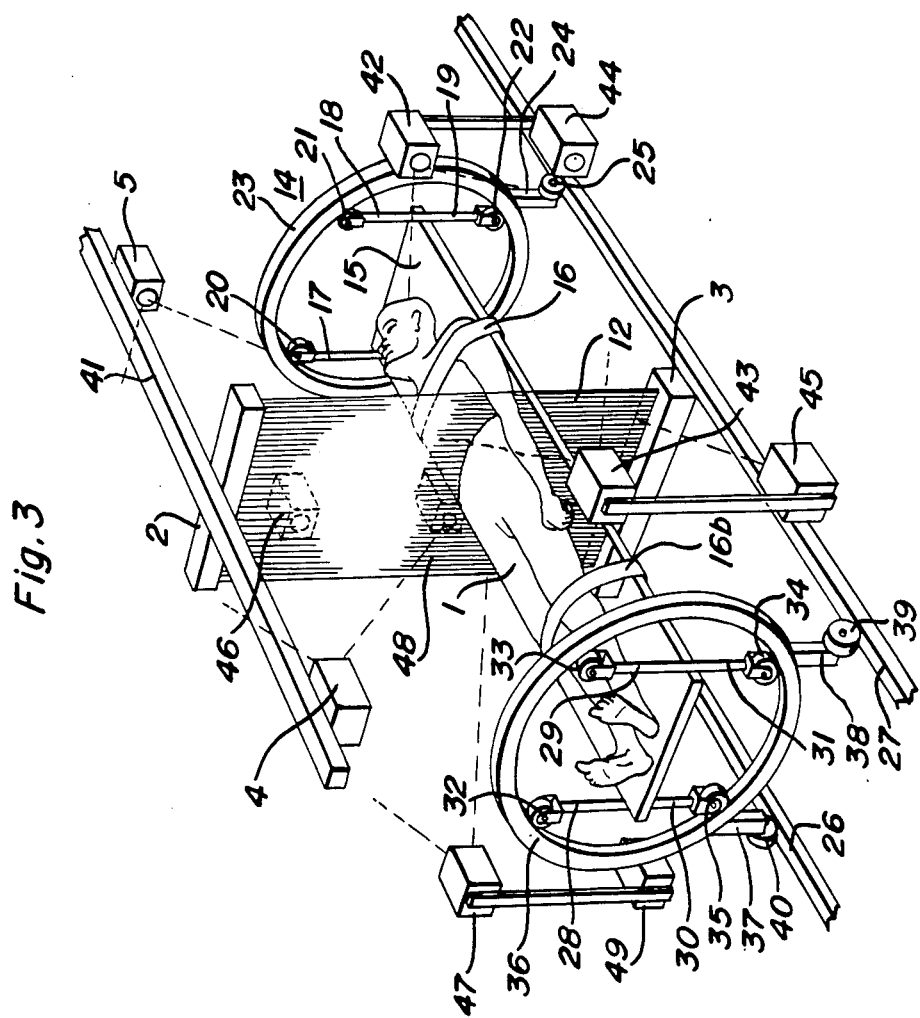
FIG. 3 shows a means for generating a circumferential line about a body, and also a means for reproducing said circumferential line.

A means according to FIG. 1 has proved extremely useful in determining the coordinates for an arbitrary point on a human body. A practical example of this is shown in FIG. 3 showing an examination table 14 with a slab 15 on which a person 1 is placed and suitably retained by means of two straps 16 and 16B. At its upper end the slab has four arms, three of which are visible, namely arms 17–19. Each arm is provided at its free end with a wheel. The three wheels for arms 17–19 are designated 20,21 and 22 and abut against the inner surface of a ring 23. The ring 23 has two legs, of which the right leg 24 is visible. Each leg is provided at its lower end with a wheel. The wheel for leg 24 is designated 25. The wheels of both legs run along two rails 26 and 27. The slab 15 is also provided at its other or lower end with four arms 28–31, also having wheels 32–35. The wheels abut against the inner surface of a ring 36 corresponding to the ring 23. The ring 36 has two legs 37 and 38, each with a wheel 39 and 40, respectively. The examination table 14 with parts 15–40 is displaceable to and fro along the rails 26 and 27. It is also pivotable about an axis constituting the normal of the mid-point of rings 23 and 36. The examination table thus permits a patient or human body 1 to be moved backwards and forwards and also in a rotary movement about an axis parallel to the longitudinal direction of the body. A rod or beam 41 is arranged above the rails 26 and 27. Two TV cameras are arranged, one at each end of the beam. These cameras face each other and are aligned parallel to the beam or rod 41. Between the two TV cameras 4 and 5 is a slot light source 2, which generates a light curtain perpendicular to the slab 15, thus forming a circumferential line over the body 1 as shown in FIG. 2. A second light source 3 is arranged below the slab 15, so that a circumferential line is form all the way round the body 1. The slab 15 is presumed to be of translucent material. Two cameras 4 and 5 and two slot light sources 2 and 3 are generally quite sufficient. The reproduction capability can be substantially increased by locating a number of camera pairs around the slab 15. The figure thus shows additionally four pairs of cameras, namely 42 and 43, 44 and 45, 46 and 47, and 48 and 49. Each of said pairs of cameras may be arranged along a post or beam in the same way as cameras 4 and 5. All the cameras are arranged symmetrically around the slab 15. One or more of the extra camera pairs may be supplemented by slot light sources in the same way as cameras 4 and 5. All cameras are connected to the interface unit mentioned in connection with FIG. 1. The position of the examination table 14 along the rails 26 and 27 is registered in the program unit 9.

The arrangement described above functions as follows.

It is assumed that the examination table 14 is to the left of cameras 43,45,47 and 47 and below cameras 4 and 5. In this position a patient is placed on the slab 15 and suitably strapped down. The patient is then moved continuously or in steps from left to right resulting in a number of consecutive circumferential lines occurring one after the other from head to foot of the patient's body 1. Each circumferential line is registered by cameras 4 and 5 as well as by the other cameras, too, if necessary. Each circumferential line registered by the cameras 4 and 5 generates predetermined video signals which are transmitted to the interface unit 6 where they are converted to digital signals. The digital signals are in turn transmitted to the computer 8. Here the coordinates along the registered circumferential line are calculated and then supplied to the memory unit 9.

To facilitate calculation of the coordinates it may be advisable to use the interlacing technique, only making use of alternate lines of a TV camera to calculate the coordinates.

With the arrangement shown, therefore, a number of consecutive circumferential lines can be arranged along a human body and registered, thus ensuring that complete information as to the coordinates for the body surface exists in computerised form in a memory unit. Each circumferential line can be photographed by several pairs of cameras or by only one pair, in which case the cameras must be rotated around the patient or vice versa.

All cameras with their slot light sources can be mounted as a single unit, displaceable along an examination table.

In FIG. 3 the beam 41 is parallel to the slab 15, but is must be evident that the beam 41 may be at an angle to the slab 15. The other cameras may also be similarly arranged.

The computer 8 may be arranged so that if the circumferential line 13 falls within a certain distance of the cameras an indication is obtained, such as an audible signal. This feature enables the use of light curtains generating a line around an object and a camera arrangement to notify that the object has come too close to the camera arrangement. The latter provides a collision monitor. The camera arrangement and light curtain can be arranged on a vehicle.

Figure 4:
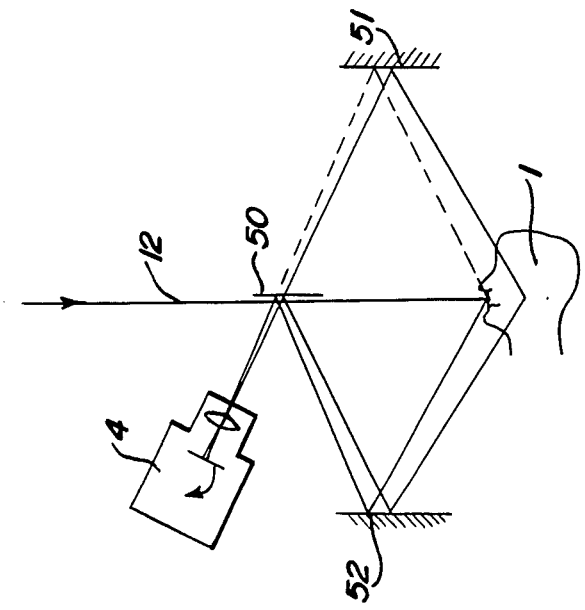
FIG. 4 shows a mirror arrangement replacing one of the cameras.

The camera 5 in the arrangement shown in FIG. 3 may be replaced by a mirror arrangement as shown in FIG. 4. One of the cameras, 4, remains in this figure which, with the aid of three mirrors 50,51 and 52 can intercept the picture intercepted by camera 5 in FIG. 3. The light curtain 12 remains in the figure, extending to a human head 1. On each side of the body, i.e. the head, are two mirrors 51 and 52 which intercept a circumferential line and reflect it on to the third mirror 50. The third mirror is of semi-translucent type. Light rays from the mirror 51 pass partly straight through mirror 50 to camera 4, whereas rays from mirror 52 are reflected partly at mirror 50 towards camera 4.

By observing a circumferential line around a ody from two directions, either using two cameras or one camera and a mirror arrangement, the advantage is gained that the obstacles perceived by one of the cameras in front of a circumferential line do not prevent reproduction of a circumferential line since the other camera observes the circumferential line without obstruction.

It should be evident that economically it is advantageous to replace one camera 5 by the three mirrors 50,51 and 52.

The means shown in FIG. 1 can also be used to register the surface structure of a road. The light curtain 12 is then arranged transversely to the longitudinal extension of the road and two or more light curtains beside each other may be necessary, with the appropriate number of cameras. A beam 41 with slot light source 2 and cameras 4 and 5 can suitably be arranged on a vehicle and, depending on the width of the road, a number of such units can be placed one beside the other to cover the width of the road.

We claim:

1. Apparatus for determining the coordinates relative to a predetermined reference system at one or more points on the external or internal contour of a body, which body may be a human body, comprising in combination:
   (a) slot light source means (2,3) for generating a light curtain (12) forming a circumferential line around a body (1) whose coordinates are to be determined.
   (b) support means (14) for orienting and positioning the body (1) relative to a predetermined reference system;
   (c) video means (4) for detecting sequentially from at least one direction a plurality of circumferential lines along a given axis of the body (1) as the body (1) and video means (4) are moved relative to one another by the support means and producing a series of signals; and
   (d) computer means (8,9) connected to the video means (4) for receiving the series of signals and determining and storing coordinates for points along each circumferential line detected.

2. Apparatus according to claim 1, wherein each of the circumferential lines is recorded from at least two directions; the video means (4) including at least two pairs of video cameras (42–47) arranged for recording at least part of each of the circumferential lines.

3. Apparatus according to claim 2, wherein each of the pairs of video cameras is arranged directed towards one another along a direction of the support means and perpendicular to the light curtain.

4. Apparatus according to claim 3, wherein each camera of each of the pairs of video cameras records all of each of the circumferential lines.

5. Apparatus according to claim 1, wherein each of the circumferential lines is recorded from at least two directions; the video means (4) including a video camera (4), and mirror means (50–52) for reflecting one of said circumferential lines toward the camera (4).

6. Apparatus according to claim 1, wherein the support means moves a body (1) whose coordinates are to be determined relative to said stationary light source means (2,3) and said video means (4).

7. Apparatus according to claim 1, wherein the support means (14) retains the video means (4) and the body (1) whose coordinates are to be determined in a predetermined relationship relative to one another, and the light source means (2,3) is movable relative to the body (1).

8. Apparatus according to claim 1, wherein the support means (14) is constructed of a translucent material.

9. Apparatus according to claim 1, wherein the light source means (2,3) generates light of a predetermined wavelength, and the video means (4) being arranged to a process only light of the predetermined wavelength.

10. Apparatus according to claim 1, wherein the computer means is arranged for indicating when any part of one of said circumferential lines exceeds predetermined limits of the reference system.

* * * * *